United States Patent [19]
Kania

[11] Patent Number: 6,042,533
[45] Date of Patent: Mar. 28, 2000

[54] APPARATUS AND METHOD FOR RELIEVING MOTION SICKNESS

[76] Inventor: Bruce Kania, P.O. Box 5186, Bozeman, Mont. 59717

[21] Appl. No.: 09/121,720

[22] Filed: Jul. 24, 1998

[51] Int. Cl.[7] .................................................. A61M 21/00
[52] U.S. Cl. ............................. 600/27; 128/897; 128/898
[58] Field of Search ........................ 600/26–28; 128/897, 128/898

[56] References Cited

U.S. PATENT DOCUMENTS

| | | |
|---|---|---|
| 1,907,402 | 5/1933 | Fedor . |
| 2,288,683 | 7/1942 | Clancy . |
| 2,745,091 | 5/1956 | Leffler . |
| 3,461,423 | 8/1969 | Trumble . |
| 3,548,400 | 12/1970 | Boyd . |
| 3,610,227 | 10/1971 | Griffin . |
| 4,052,720 | 10/1977 | McGregor et al. . |
| 4,070,463 | 1/1978 | Graybiel . |
| 4,283,798 | 8/1981 | Kuehn . |
| 4,284,987 | 8/1981 | Gibson et al. . |
| 4,508,510 | 4/1985 | Clifford . |
| 4,562,589 | 12/1985 | Warnaka et al. . |
| 4,777,170 | 10/1988 | Heinrich . |
| 4,817,149 | 3/1989 | Myers . |
| 4,817,633 | 4/1989 | McStravick et al. . |
| 4,925,878 | 5/1990 | Bodó et al. . |
| 4,929,228 | 5/1990 | Hendricks . |
| 4,930,435 | 6/1990 | Newman . |
| 4,992,443 | 2/1991 | Chelen . |
| 5,067,941 | 11/1991 | Hendricks . |
| 5,119,754 | 6/1992 | Martinez et al. . |
| 5,120,739 | 6/1992 | Chelen . |
| 5,143,081 | 9/1992 | Young et al. . |
| 5,161,196 | 11/1992 | Ferguson . |
| 5,209,712 | 5/1993 | Ferri . |
| 5,303,715 | 4/1994 | Nashner et al. . |
| 5,353,242 | 10/1994 | Crosbie et al. . |
| 5,425,378 | 6/1995 | Swezey et al. . |
| 5,603,334 | 2/1997 | Sharp . |

(List continued on next page.)

OTHER PUBLICATIONS

Discovery, vol. 14, No. 19, Oct. 5, 1990, Brooks AFB, Texas, "Study Opens Ears on 3–D Sound" By Capt Alvin Mitchell, Ask Office of Public Affairs Wright–Patterson AFB, Ohio.

AOPA Pilot, Dec. 1989, pp. 65–69, "The Art of Noise", "Technology brings tranquility to the cockpit", By Marc E. Cook.

Technology, Time, Dec. 4, 1989, p. 94, "Fighting Noise with Antinoise", Electronic mufflers cancel unwanted sound waved in midair, By Philip Elmer–Dewitt.

Aviation, Space, and Environmental Medicine, Aug. 1989, pp. 779–785, "Performance and Well–being Under Tilting Conditions: The Effects of Visual Reference and Artificial Horizon" By A. Rolnick, Ph.D., and W. Bless, Ph.D.

Aviation, Space, and Environmental Medicine, Aug. 1990, pp. 699–706, "The Effects of Acoustic Orientation Cues on Instrumental Flight Performance in a Flight Simulator" By Terence J. Lyons, M.D., M.P.H., Ken K. Gillingham, M.D., Ph.D., Don C. Teas, Ph.D., William R. Ercoline, M.S., and Carolyn Oakley, B.A.

Comparative Studies of Hearing in Vertebrates, Popper, An., Fay, R.R.(eds). New York, Springer–Verlag, 1980, pp. 357–373, Chapter 12, "Directional Hearing in Terrestrial Mammals", By George Gourevitch of the Department of Psychology, Hunter College of the City University of New York.

*Primary Examiner*—Samuel Gilbert
*Attorney, Agent, or Firm*—Oblon, Spivak, McClelland, Maier & Neustadt, P.C.

[57] ABSTRACT

A method and apparatus used for relieving motion sickness. The apparatus includes a sensor which detects a motion of an object and a sensory converter coupled to the sensor and configured to convert the detected motion to corresponding sensory signals for presentation to a user. In addition, the sensory signals have a variation in spectral emphasis in proportion to the detected motion. The sensory signals include video, audio and white noise signals and resolve a conflict between vestibular, ocular, and proprioceptive inputs of the user, thus relieving motion sickness.

24 Claims, 5 Drawing Sheets

U.S. PATENT DOCUMENTS

| | | |
|---|---|---|
| 5,613,690 | 3/1997 | McShane et al. . |
| 5,629,848 | 5/1997 | Repperger et al. . |
| 5,645,077 | 7/1997 | Foxlin ................................. 600/597 |
| 5,647,835 | 7/1997 | Martineau . |
| 5,694,939 | 12/1997 | Cowings ................................. 128/905 |
| 5,807,284 | 9/1998 | Foxlin ................................. 600/595 |
| 5,829,446 | 11/1998 | Tiffany ................................. 128/898 |

APPARATUS AND METHOD FOR RELIEVING MOTION SICKNESS

BACKGROUND OF THE INVETION

1. Field of the Invention

The present invention relates to a method and apparatus for relieving motion sickness. More particularly, the present invention is related to providing an individual with an array of video, audio, and white noise sensory signals so that the individual may use these signals to improve a sense of equilibrium.

2. Discussion of the Background

Essentially, motion sickness occurs as a result of an unusual motion experience. When a person is unable to predict or anticipate this unusual motion, the person's equilibrium may be effected. The phenomenon of motion sickness may be derived from a principle researched by Dr. David Winters, a retired University of Waterloo professor, and which is referred to as "The Principle of Indeterminacy."

The principle of indeterminacy describes a human's natural ability to identify changes in the neuromuscular skeletal system and to adapt to a new optimum motion. For example, if a prosthetic leg does not offer comparable function, an amputee will favor the remaining leg. Thus, the residual limb becomes weaker and the remaining leg becomes stronger. The option to utilize the prosthesis or the natural leg represents a conflict, i.e., between walking in a conventional symmetrical manner or favoring the natural leg. The person, without conscious volition, chooses favoring the natural side when the choice is perceived by the human's body as optimal. Currently, it is not known for certain which senses are most influential in making this choice. However, it is likely that pain and comfort, proprioceptive, vestibular, and ocular inputs affect this choice.

Similarly, motion sickness results from a conflict between these vestibular, ocular and proprioceptive inputs. For example, conventional wisdom among charter boat operators is that charter boat captains do not get seasick, unless they spend a significant amount of time below deck, whereas captains of cruise ships are known to be somewhat more susceptible to motion sickness. This is because a charter boat captain usually sits high in the cabin, a position from where he can observe quite clearly what the relatively small charter boat is about to experience. Thus, he has accurate visual data which reconciles a conflict between the vestibular, ocular, and proprioceptive inputs. On the contrary, the captain of a large cruise ship cannot see what is taking place immediately in front of the ship's bow. Thus, a conflict between the vestibular, ocular, and proprioceptive data is not resolved.

Motion sickness is very costly for many industries. For example, the airline industry loses millions of dollars per year from passengers who are unwilling to travel because they experience motion sickness. The same can be said for cruise ships. In addition, if a person experiences motion sickness while operating a dangerous vehicle, injury or even a loss of life may occur.

Thus, a need for a device which relieves motion sickness will have a significant impact on society. One proposed motion sickness device is that described in Ferguson (U.S. Pat. No. 5,161,196). Ferguson discloses positioning an array of sound emitters at the sides of an enclosure and varying the sound levels from selected emitters in response to changes in the enclosure's movement. To an individual, the sound source is not perceived as rolling with the vehicle but rather is inertially stable while the vehicle rouls relative to the sound source. That is, Ferguson is directed to creating an artificial sound horizon which is acoustically perceivable to the individual and continuously maintaining the sound horizon substantially positionally stationary with reference to a fixed horizon of the enclosure.

However, one problem with Ferguson is that an artificial sound horizon is created. This artificial sound horizon (i.e., between sound emitters at opposite sides of the enclosure) may cause an individual to experience further motion sickness because a conflict is created between the vestibular, ocular, and proprioceptive inputs and the artificial sound horizon. Further, another problem with Ferguson is that an array of sound emitters (e.g., speakers) placed at specific locations chosen in accordance with a predicted motion of the enclosure are required. That is, the speakers are required to be located in opposite sides of the enclosure.

SUMMARY OF THE NVENTION

Accordingly, an object of the present invention is to provide a novel apparatus and method for relieving motion sickness.

Another object of the present invention is to relieve motion sickness by presenting a user with any one of an audio signal, a video signal, a white noise signal, or combinations thereof which have a variation in spectral emphasis in proportion to a detected motion of an object, so that the user may resolve a conflict between vestibular, ocular, and proprioceptive inputs.

Yet another object of the present invention is to provide a device for assisting an individual which suffers from a severe vestibular imbalance by presenting this individual with audio and white noise sensory signals corresponding to a detected motion of the individual.

Still another object of the invention is to provide a device for assisting a blind individual by presenting this individual with audio and white noise signals, along with a proximity sensory signals to assist the individual in determining their relative position to other objects.

These and other objects of the present invention are achieved by providing an apparatus which includes a sensor which detects a motion of an object and a sensory converter which converts the detected motion to corresponding sensory signals. The sensory signals have a variation in a spectral emphasis in proportion to the detected motion. In addition, the sensory signals are presented to a user by using, for example, a transmitter and receiver. Thus, the user receives the sensory signals and is able to resolve a conflict between vestibular, ocular, and proprioceptive inputs via the principle of indeterminacy. The sensory signals may be any one of audio, white noise or video signals. In the case of audio signals, the variation in spectral emphasis includes varying a frequency of, for example, a first signal within a first predetermined range around a first center frequency in proportion to a detected pitching motion of the object. For the case of white noise signals, the variation in spectral emphasis includes varying, for example, a first frequency range of a the white noise signals in proportion to a detected pitching motion of the object. Finally, for the case of video signals, the variation in spectral emphasis includes varying the red, green, and blue colors used in a conventional video display. These colors are altered in proportion to the detected motion of the object.

BRIEF DESCRIPTIONS OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
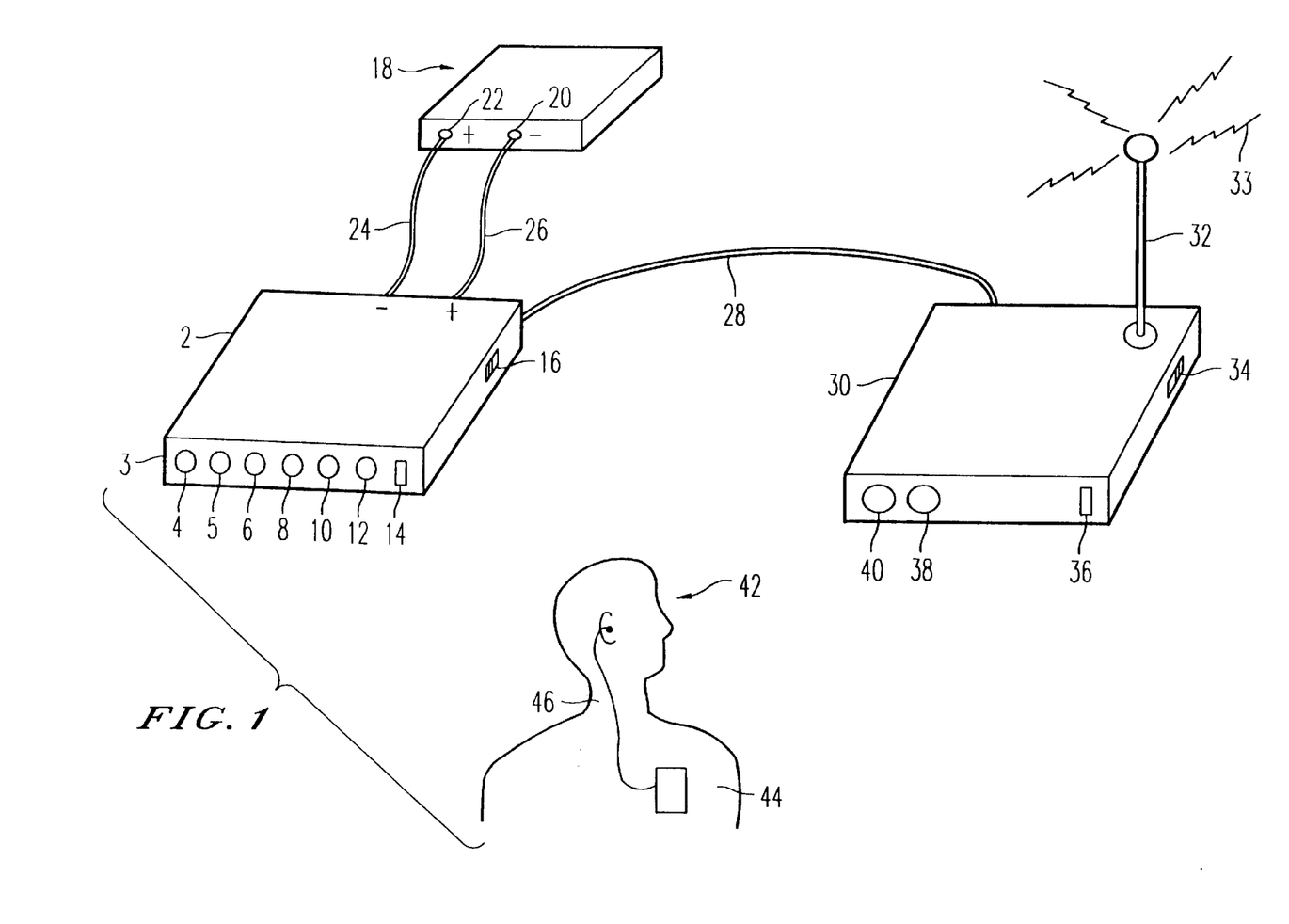
FIG. 1 is a perspective view of an apparatus for relieving motion sickness according to the present invention.

Referring now to the drawings, wherein like reference numerals designate identical or corresponding parts throughout the several views, and more particularly to FIG. 1 thereof there is illustrated an apparatus for relieving motion sickness including an inertia processor 2 connected to an external battery 18 and a transmitter 30. Also shown is a receiver 44 attached to an individual 42 for receiving a sensory signal 33 transmitted by the transmitter 30. The inertia processor 2 includes a front panel 3 which houses an audio volume control mechanism 4, a video control mechanism 5, a white noise volume control mechanism 6, a pitch (x-axis) sensitivity control mechanism 8, a yaw (y-axis) sensitivity control mechanism 10, and a vertical (z-axis) sensitivity control mechanism 12.

The audio volume mechanism 4 and the white noise volume mechanism 5 may be used to adjust the volume of the sensory signal 33 transmitted by the transmitter 30. The pitch sensitivity mechanism 8, the yaw sensitivity mechanism 10, and the vertical sensitivity mechanism 12 may be used to adjust the corresponding sensitivity of the inertia processor 2. That is, using these sensitivity mechanisms, a user may set the inertia processor 2 to be more or less sensitive in detecting a motion of an object. Also included in the front panel 3 is an LED power indicator 14 which indicates whether the power is on or off. For example, if the power is on, the LED indicator 14 will be a green color. On a side portion of the inertia processor 2 is a power switch 16 used to turn on and off the inertia processor 2. The inertia processor 2 also includes three RCA autojacks on a rear side of the instrument (not shown) which provide high impedance, low level output for audio, video and white noise signals.

The battery 18 includes a negative battery terminal 20 and a positive battery terminal 22 which connect to the inertia processor 2 via battery wires 24 and 26. In addition, the inertia processor 2 is connected to the transmitter 30 using a communication cable 28. Alternatively, the audio processor 2 may be optically connected (e.g., using infrared signals) to the transmitter 30. The transmitter 30 includes an antenna 32, a power switch 34, and a power LED indicator 36. Also included is, for example, a multichannel control mechanism 38 and a volume control mechanism 40.

The control mechanisms (e.g., volume control mechanisms 4 and 6) are not limited to the locations shown in FIG. 1. For example, the volume control mechanism 4 may be placed on a side or top portion of the inertia processor 2. Further, the battery 18, inertia processor 2, transmitter 30, and receiver 44 may be included in a single common housing.

The inertia processor 2 may be mounted or placed on a level (normally level) surface of an object. The inertia processor 2 detects a motion of the object and converts this motion to corresponding sensory signals for presentation to a user. The sensory signals have a variation in spectral emphasis in proportion to the detected motion. For example, if the inertia processor 2 is configured to operate using audio signals, i.e., by connecting the audio output jack of the inertia processor 2 to the transmitter 30, the variation in spectral emphasis includes varying a frequency of, for example, a first signal within a first predetermined range around a first center frequency in proportion to a detected pitching motion of the object. Alternatively, if the inertia processor 2 is configured to operate using white noise signals, the variation in spectral emphasis includes varying, for example, a first frequency range of the white noise signals in proportion to a detected pitching motion of the object. Finally, if the inertia processor 2 is configured to operate using video signals, the variation in spectral emphasis includes varying the red, green, and blue colors used in a conventional video display. The red, green and blue colors are altered in proportion to the detected motion of the object.

The sensory signals detected by the inertia processor 2 are presented to the user 42 using, for example, the transmitter 30 and receiver 44. The receiver 44 may be, for example, a pocket-sized receiver, in order to receive the detected sensory signals 33. The receiver 44 also includes, for example, an earphone 46 so the user may listen to the corresponding sensory signals. The user 42 then uses the sensory signals 33 transmitted by the transmidtter 30, without conscious volition, to resolve a conflict between the vestibular, ocular, and propreoceptive inputs, thereby relieving a sense of motion sickness.

In addition, it should be noted that FIG. 1 illustrates the detected sensory signals being presented to the user 42 with a transmitter 30 and receiver 44. However, it is also possible to present the sensory signals detected by the inertia processor 2 directly to the user 42 by using an earphone, for example, connected to the inertia processor 2. That is, the use of a separate transmitter 30 and receiver 44 is not required.

Figure 2:
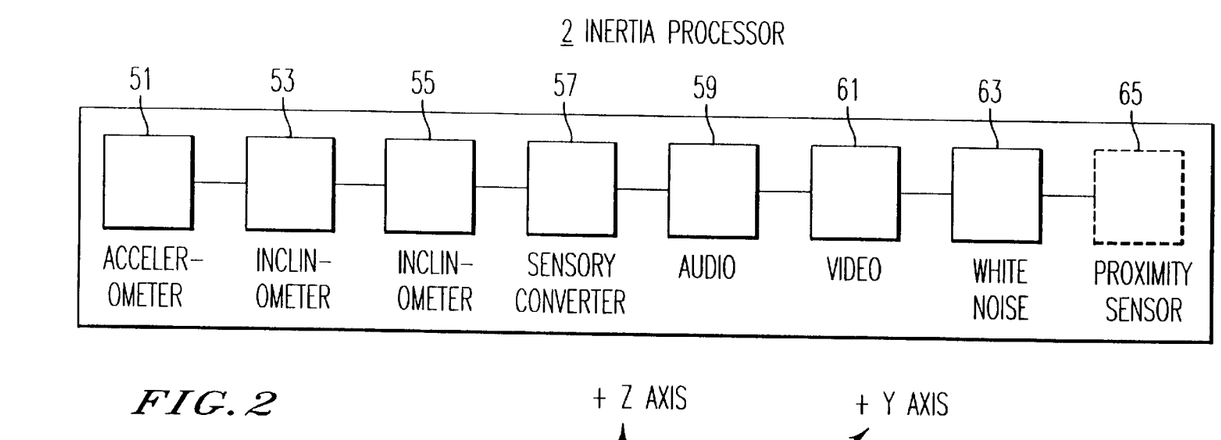
FIG. 2 is a block diagram illustrating the components of an inertia processor/sensor device according to the present invention.

FIG. 2 illustrates a block diagram of the components contained within the inertia processor 2. As shown, the inertia processor 2 includes an accelerometer 51, a first inclinometer 53, a second inclinometer 55, a sensory converter 57, an audio processor 59, a video processor 61, a white noise processor 63, and optionally a proximity sensor 65.

Figure 10:
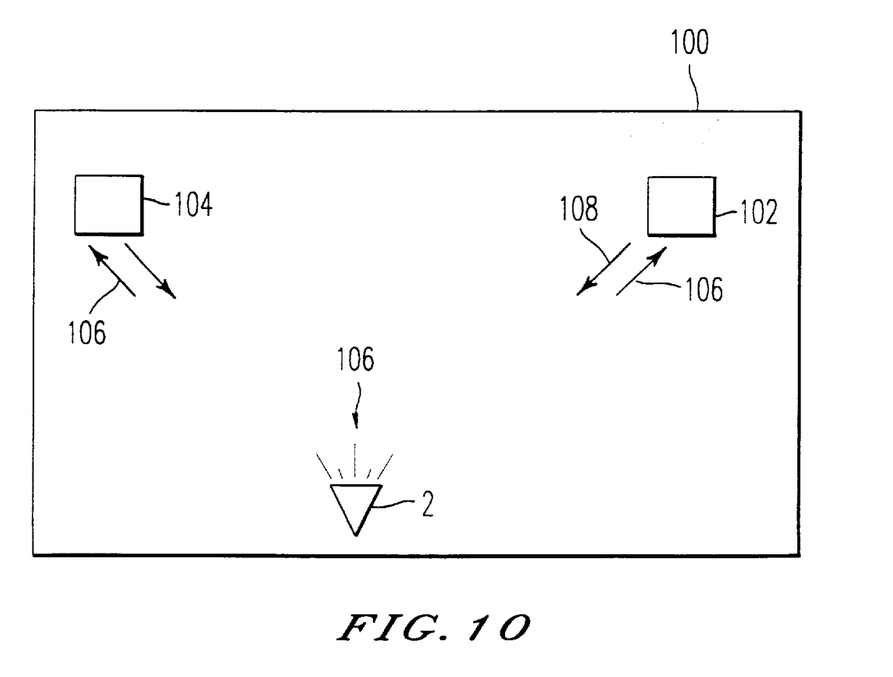
FIG. 10 is another perspective view of the motion sickness device being used to assist an eyesight impaired individual.

The accelerometer 51, and inclinometers 53 and 55 may be those which are commercially available. The accelerometer 51 detects a vertical motion of an object, the first inclinometer 53 detects a yaw motion of the object, and the second inclinometer 55 detects a pitching motion of the object. The sensory converter 57 converts this detected motion to corresponding sensory signals for presentation to the user. The audio processor 59 communicates the sensory signals as audio signals to the transmitter 30. Similarly, the video processor 61 and white noise processor 63 communicate the sensory signals as video signals and white noise signals, respectively, to the transmitter 30. In addition, the inertia processor 2 may include an additional accelerometer and a third and fourth inclinometer so that the inertia processor may detect a motion in at least one of six degrees of freedom. The inclinometers and accelerometers function as a sensor which detect a motion of the object. Further, the inertia processor 2 may optionally include a proximity sensor 65. The proximity sensor 65 determines relative locations of other objects with respect to the inertia processor 2 (e.g., by using lasers, or capacitive sensor systems). Thus, a blind person could wear the inertia processor 2 including the proximity sensor 65 and receive audio signals corresponding to the determined relative position of other objects. This feature is shown in FIG. 10 and will be discussed later.

Figure 3:
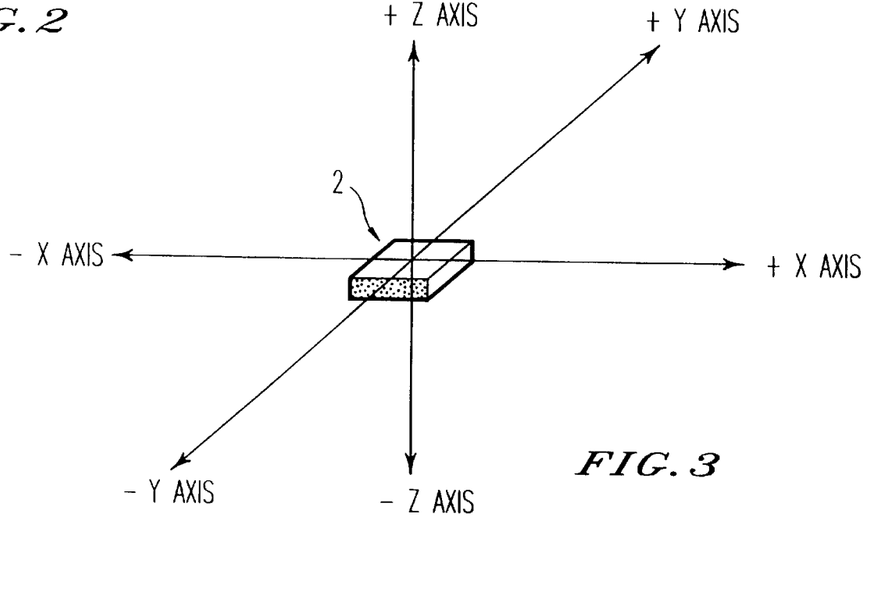
FIG. 3 illustrates a three-dimensional axis with respect to the inertia processor according to the present invention.

FIG. 3 illustrates a three-dimensional axis with respect to the inertia processor 2 shown in FIG. 2. The accelerometer 51 detects a vertical motion of the object along the vertical axis, designated as the z-axis. The inclinometers 53 and 55 detect inclination changes (i.e., pitching and yawing motions) about the horizontal plane designated as the x-axis and y-axis, respectively.

Figure 4:
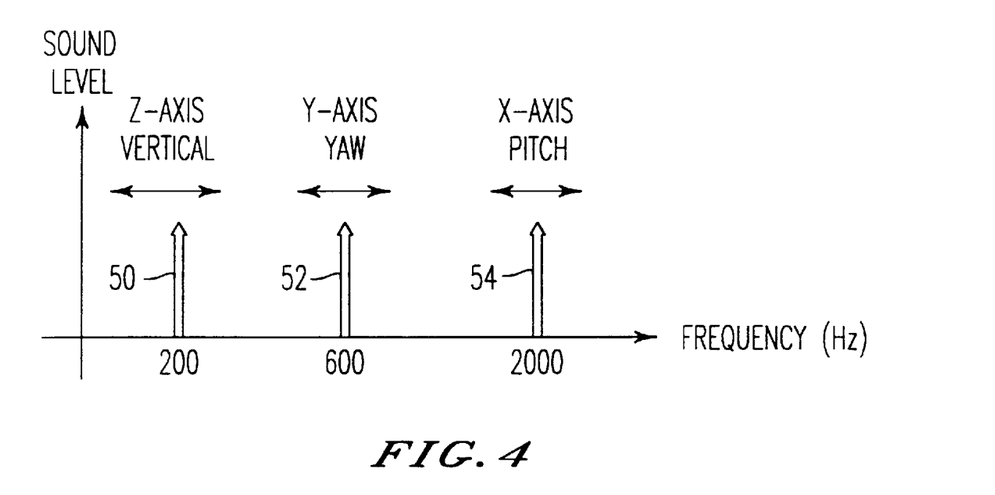
FIG. 4 is a graph illustrating frequencies of audio signals corresponding to vertical, yaw, and pitch motions detected by the inertia processor shown in FIG. 3.

FIG. 4 illustrates audio signals in response to motion detected by the inertia processor 2. As shown, the inertia processor 2 generates three different audio signals which individually change frequency in response to a detected motion. The z-axis frequency tone 50, which may be centered at 250 Hz, for example, increases in frequency when a positive z-axis motion is detected and decreases in frequency in response to a negative z-axis detected motion. The z-axis vertical tone 50 shown in FIG. 4 is at 200 Hz which represents a decrease of 50 Hz from the center frequency. That is, a negative z-axis motion was detected by the accelerometer 51. The y-axis frequency tone 52, centered at 500 Hz, for example, increases in frequency when the instrument is tilted clockwise (when viewed from the front of the device) about the y-axis. This is referred to as a yaw to the right. In addition, the y-axis frequency tone 52 decreases in frequency when the instrument is tilted counterclockwise about the y-axis, referred to as a yaw to the left. The y-axis frequency tone 52 shown in FIG. 4 is at 600 Hz which represents an increase of 100 Hz from the center frequency. That is, a yaw to the right was detected by the inclinometer 53. The x-axis frequency tone 54, centered at 2 KHz, for example, increases in frequency when the instrument is tilted forward, referred to as a forward pitch, and decreases in frequency when the instrument is tilted backwards, referred to as a rearward pitch. Thus, as shown, the x-axis frequency tone 54 has not changed, which indicates the second inclinometer 55 did not detect a pitching motion. In addition, the changes to the tone frequencies are proportional to the detected motion, that is the greater the detected motion, the greater the tone change. However, the proportional relationship is not necessarily linear and may be empirically determined The representation of the center tone frequencies of 250 Hz, 500 Hz, and 2 KHz are for illustration purposes only and other values may be used.

Further, FIG. 4 corresponds to motion detected in three degrees of freedom. As discussed above, the inertia processor 2 may detect motion in at least six degrees of freedom. Thus, if six degrees of freedom were detected, it is possible to represent this by six tones rather than three tones.

Figure 5:
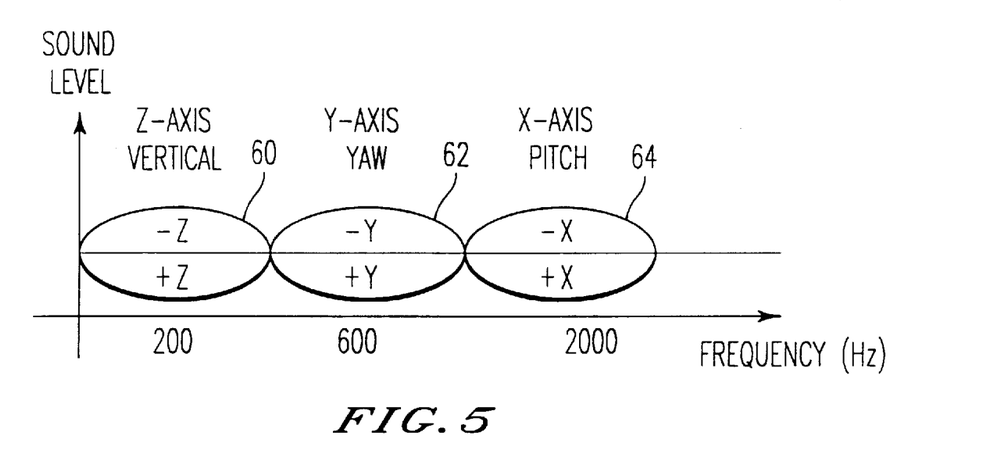
FIG. 5 is a graph illustrating frequency ranges of a white noise signal corresponding to vertical, yaw and pitch motions detected by the inertia processor shown in FIG. 3.

FIG. 5 is similar to FIG. 4 but illustrates a white noise frequency spectrum in response to motion detected by the inertia processor 2. White noise is a random noise a containing all frequencies and sounds similar to the "hiss" noise generated by an FM radio receiver when tuned off station. As shown, the spectral component of the white noise frequency spectrum is divided into three frequency ranges. The white noise frequency spectrum includes a z-axis vertical frequency range 60, a y-axis yaw frequency range 62, and an x-axis pitch frequency range 64. The amplitude of these frequency ranges are altered by the inertia processor 2 in response to the detected motion. A positive z-axis sensation decreases the amplitude of the z-axis vertical frequency range 60. A negative z-axis sensation increases the amplitude of the z-axis vertical frequency range 60. A yaw to the right decreases the amplitude of the y-axis yaw frequency range 62 and a yaw to the left increases the amplitude of this range. Similarly, a forward pitch results in a decrease of the amplitude of the x-axis pitch frequency range 64 and a rearward pitch results in an increase in amplitude of this frequency range. In addition, the changes to the amplitudes of the frequency ranges of the white noise are proportional to detected motion, that is the greater the sensation, the greater the spectral amplitude change. Again, the proportional relationship is not necessarily linear.

FIG. 5 illustrates the z-axis vertical frequency range 60, y-axis yaw frequency range 62, and x-axis pitch frequency range 64 as being centered at 200 Hz, 600 Hz, and 2 KHz, respectively. However, these ranges may be centered at other frequencies. Further, the width of the frequency ranges may be selected different than that shown in FIG. 5. In addition, FIG. 5 corresponds to motion detected in three degrees of freedom. However, as discussed above, the inertia processor 2 may detect motion in at least six degrees of freedom, and accordingly it is possible to represent these six degrees of freedom by using six frequency ranges of the white noise signal.

Figure 6:
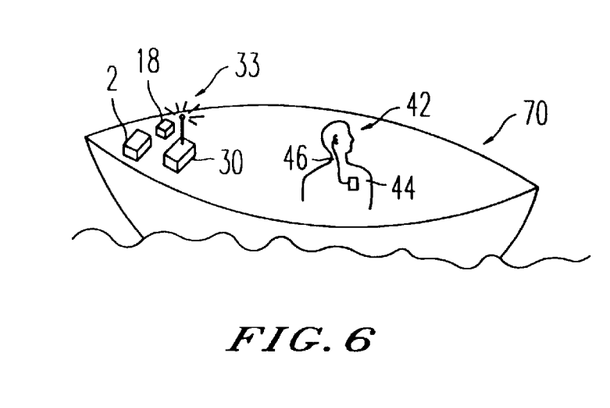
FIG. 6 is a perspective view of the motion sickness apparatus being used aboard a ship.

To operate the device of the present invention, the inertia processor may be mounted or placed on a level (normally level) surface of an object and connected to the transmitter 30. One example of using the device of the present invention is that shown in FIG. 6. As shown, the inertia processor 2, battery 18, and transmitter 30 are mounted securely in a bow of a boat 70. When the boat 70 moves, the inertia processor 2 detects this motion and converts the detected motion into corresponding sensory signals. The sensory signals 33 are then transmitted to the receiver 44 which is attached to the user 42. The user 42 hears the sensory signals 33 using, for example, an earphone 46. Thus, the user will, without conscious volition, utilize this accurate new data stream to resolve the conflict between the various ocular, vestibular and proprioceptive inputs via the principle of indeterminacy. The sensory signals 33 may be audio or white noise signals. An example of using video sensory signals is shown in FIG. 9 and will be described later.

Figure 7:
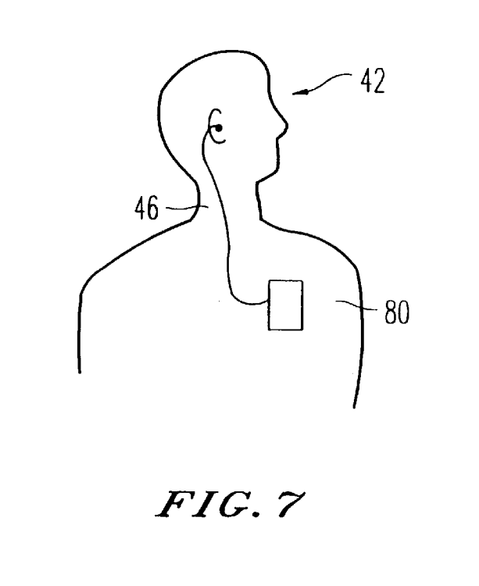
FIG. 7 is a perspective view of the motion sickness apparatus attached to an individual.

FIG. 7 illustrates another use of the device according to the present invention. In this example, the inertia processor 2, battery 18, transmitter 30, and receiver 44 are contained in a single common housing 80. The inertia processor 2 is similar to that shown in FIG. 2, but includes only the first inclinometer 53 and second inclinometer 55 which detect yaw and pitch motions, respectively (i.e., the accelerometer 51 is not included). Thus, the inertia processor 2 contained in the common housing 80 detects changes in the individual's motion (i.e., y-axs yaw and x-axis pitch motions), converts this detected motion to corresponding sensory signals, and presents the signals to the user. Further, the device may be placed at various points on the body to accurately reflect positional changes, such as a plurality of sensors placed along the individual's spine.

Figure 8:
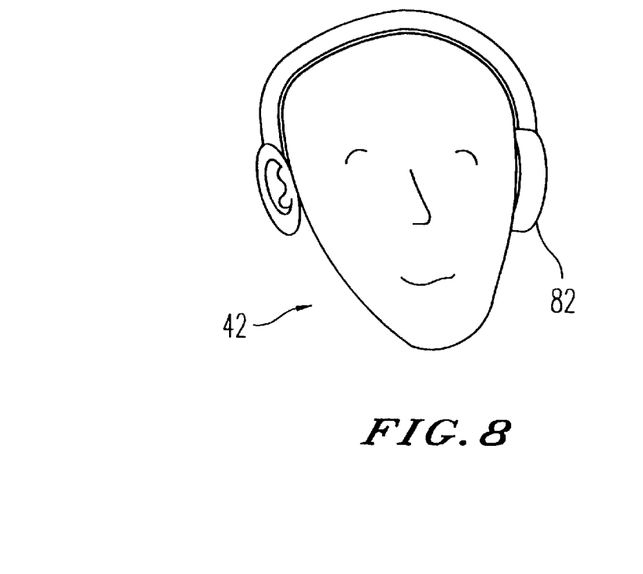
FIG. 8 is another perspective view of the motion sickness apparatus included within a headphone.

FIG. 8 illustrates yet another example in which the device of the present invention may be used. In this example, the inertia processor 2, battery 18, transmitter 30, and receiver 44 are included in a headset so that the movement of the head is detected rather than the movement of the body. The inertia processor 2 is similar to that discussed for FIG. 7 and detects motion in 2 axes (i.e., yaw and pitch).

Figure 9:
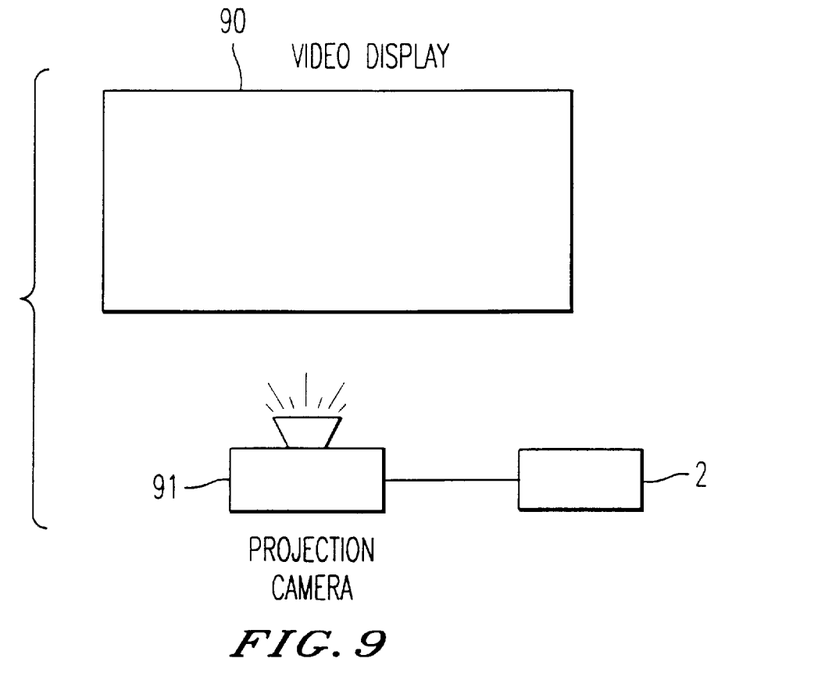
FIG. 9 is yet another perspective view of the motion sickness device being used to project a video image on a display.

FIG. 9 illustrates another example in which the device may be used. In this example, the inertia processor 2 detects the motion of an object and converts this detected motion into a video signal which may be displayed on a video display 90. The converted video signal corresponding to the detected motion is output to, for example, a projection camera 91 via the audio jack of the inertia processor 2. The projection camera 91 projects the video signal to a video display 90, which a single user or multiple users may be viewing while being aboard, for example, a ship. The video signal displayed may be a variety of colors, each color corresponding to a particular detected motion. For example, the red, green and blue colors in a conventional color scheme may correspond to a detected vertical, pitch, and yaw motion of the object. In addition, each of the selected colors may vary in spectral emphasis in proportion to the detected motion. Thus, the individual user or multiple users viewing the display, can use this video image to reconcile a conflict between the vestibular, ocular, and proprioceptive inputs, thus reducing the likelihood of motion sickness. Similarly, a video signal representation of the actual ship, for example, as in a view directly forward from the bow will also accomplish this same conflict resolution.

FIG. 10 illustrates another example in which the device of the present invention may be used. In this example, the device is used to assist a blind person. Essentially, if one closes their eyes and walks around a room, it is not particularly difficult to maintain a vertical position. Their proprioceptive receptors and to some extent their vestibular receptors may be termed an experimental data base which allows them to understand where they are relative at least to an upright position. But if an individual has been blind since birth, they would not have access to this experimental data base. The device according to the present invention is used to expand this data base. By verifying where an individual's body is relative to the ground and other objects, the individual in question could move about with more confidence. Thus, by using the proximity sensor 65 (shown in FIG. 2), the individual will have an added ability to assert their position relative to other objects.

FIG. 10 illustrates a room 100 in which a blind person (not shown) is wearing the inertia processor 2 included in the common housing 80 shown in FIG. 7, for example. Also shown are objects 102 and 104 which may be furniture, another person, etc. Thus, as the individual walks about the room, the proximity sensor 65 transmits, for example, laser signals 106. The laser signals 106 are then reflected off the objects 102 and 104. For example, as shown, a reflected signal 108 is reflected off the object 102. The inertia processor 2 receives this reflected signal 108 and converts it to an audio signal. The audio signals have a spectral emphasis which varies in proportion to the distance of the detected objects relative to the blind individual. For example, if the object 102 is very close, a high pitch tone may be generated, whereas if the object 102 in far away, and low pitch tone may be used.

A method of relieving motion sickness will now be described with reference to FIGS. 1, 3 and 4. The inertia processor 2 is used for detecting a motion of an object and for converting the detected motion to corresponding sensory signals. The sensory signals have a variation in spectral emphasis in proportion to the detected motion. Further, the method of converting includes presenting the sensory signals using, for example, the transmitter 33 and the receiver 44. In one example, the method of converting includes varying a frequency of a first signal within a first predetermined range around a first center frequency in proportion to a detected pitching motion of the object, and varying a frequency of a second signal within a second predetermined range around a second center frequency in proportion to a detected yawing motion of the object. In another example, the method of converting includes varying a spectral emphasis of a first frequency range of a white noise signals in proportion to a detected pitching motion of the object, and varying a spectral emphasis of second frequency range of the white noise signals in proportion to a detected yawing motion of the object. In addition, the method of converting also includes generating video signals which correspond to the detected sensory signals.

Further, the present inventor has determined that low frequency horizontal movements appear to be most related to motion sickness. By providing a device which includes a sensor to detect these movements, and a sensory converter coupled to the sensor, as discussed above, the present invention reduces the effect of motion sickness.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent in the United States is:

1. An apparatus for relieving motion sickness, comprising:
    a sensor which detects a motion of an object;
    a sensory converter coupled to said sensor and configured to convert said detected motion to corresponding sensory signals, said sensory signals having a variation in spectral emphasis in proportion to said detected motion; and
    a presentation mechanism configured to present said sensory signals to a user.

2. The apparatus according to claim 1, wherein said sensor detects said motion in at least one of six degrees of freedom.

3. The apparatus according to claim 1, wherein said sensory converter comprises:
    a first mechanism configured to vary a frequency of a first signal within a first predetermined range around a first center frequency in proportion to a detected pitching motion of said object; and
    a second mechanism configured to vary a frequency of a second signal within a second predetermined range around a second center frequency in proportion to a detected yawing motion of said object.

4. The apparatus according to claim 1, wherein said sensory converter comprises:
    a first mechanism configured to vary a frequency of a first signal within a first predetermined range around a first center frequency in proportion to a detected vertical motion of said object;
    a second mechanism configured to vary a frequency of a second signal within a second predetermined range around a second center frequency in proportion to a detected yawing motion of said object; and a third mechanism configured to vary a frequency of a third signal within a third predetermined range around a third center frequency in proportion to a detected pitching motion of said object.

5. The apparatus according to claim 1, wherein said sensor, said sensory converter, and said presentation mechanism are included in a common housing.

6. The apparatus according to claim 1, said presentation mechanism comprises at least one of an earphone, headphone, speaker, and video display.

7. The apparatus according to claim 1, wherein said sensory converter comprises a mechanism configured to generate video signals which correspond to said sensory signals.

8. The apparatus according to claim 1, wherein said sensory converter comprises a mechanism configured to generate audio signals which correspond to said sensory signals.

9. The apparatus according to claim 1, wherein said sensory converter comprises a mechanism configured to generate white noise signals which correspond to said sensory signals.

10. The apparatus according to claim 9, wherein said sensory converter comprises:

a first mechanism configured to vary a spectral emphasis of a first frequency range of a said white noise signals in proportion to a detected pitching motion of said object; and a second mechanism configured to vary a spectral emphasis of second frequency range of said white noise signals in proportion to a detected yawing motion of said object.

11. The apparatus according to claim 9, wherein said sensory converter comprises:

a first mechanism configured to vary a spectral emphasis of a first frequency range of a said white noise signals in proportion to a detected vertical motion of said object;

a second mechanism configured to vary a spectral emphasis of second frequency range of said white noise signals in proportion to a detected yawing motion of said object; and a third mechanism configured to vary a spectral emphasis of third frequency range of said white noise signals in proportion to a detected pitching motion of said object.

12. The apparatus according to claim 1, wherein said sensor comprises a plurality of sensors to be attached to said user.

13. The apparatus according to claim 1, further comprising:

a proximity sensor coupled to said sensory converter and configured to detect a relative location of other objects.

14. A method for relieving motion sickness, comprising:

detecting a motion of an object;

converting said motion detected in said step of detecting to corresponding sensory signals, said sensory signals having a variation in spectral emphasis in proportion to said detected motion; and presenting said sensory signals to a user.

15. The method according to claim 14, wherein said step of detecting detects said motion in at least one of six degrees of freedom.

16. The method according to claim 14, wherein said step of converting further comprises:

varying a frequency of a first signal within a first predetermined range around a first center frequency in proportion to a detected pitching motion of said object; and varying a frequency of a second signal within a second predetermined range around a second center frequency in proportion to a detected yawing motion of said object.

17. The method according to claim 14, wherein said step of converting comprises:

varying a frequency of a first signal within a first predetermined range around a first center frequency in proportion to a detected vertical motion of said object;

varying a frequency of a second signal within a second predetermined range around a second center frequency in proportion to a detected yawing motion of said object; and varying a frequency of a third signal within a third predetermined range around a third center frequency in proportion to a detected pitching motion of said object.

18. The method according to claim 14, wherein said step of presenting presents said sensory signals to said user using at least one of an earphone, headphone, speaker, and video display.

19. The method according to claim 14, wherein said step of converting comprises:

generating video signals which correspond to said sensory signals.

20. The method according to claim 14, wherein said step of converting comprises:

generating audio signals which correspond to said sensory signals.

21. The method according to claim 14, wherein said step of converting comprises:

generating white noise signals which correspond to said sensory signals.

22. The method according to claim 21, wherein said step of converting further composes:

varying a spectral emphasis of a first frequency range of a said white noise signals in proportion to a detected pitching motion of said object; and varying a spectral emphasis of second frequency range of said white noise signals in proportion to a detected yawing motion of said object.

23. The method according to claim 21, wherein said step of converting comprises:

varying a spectral emphasis of a first frequency range of a said white noise signals in proportion to a detected vertical motion of said object;

varying a spectral emphasis of second frequency range of said white noise signals in proportion to a detected yawing motion of said object; and varying a spectral emphasis of third frequency range of said white noise signals in proportion to a detected pitching motion of said object.

24. The method according to claim 14, further comprising:

detecting a relative location of other objects; and converting said detected relative motion to said corresponding sensory signals.

* * * * *